United States Patent
Toth et al.

[11] Patent Number: 5,361,291
[45] Date of Patent: Nov. 1, 1994

[54] DECONVOLUTION FILTER FOR CT SYSTEM

[75] Inventors: Thomas L. Toth, Brookfield; Carl R. Crawford, Milwaukee; Kevin F. King, New Berlin, all of Wis.

[73] Assignee: General Electric Company, Milwaukee, Wis.

[21] Appl. No.: 796,113

[22] Filed: Nov. 20, 1991

[51] Int. Cl.[5] .......................................... G01N 23/083
[52] U.S. Cl. ...................... 378/12; 378/901; 364/413.21
[58] Field of Search .................... 378/12, 11, 901; 364/413.14, 413.21

[56] References Cited

U.S. PATENT DOCUMENTS

| | | | |
|---|---|---|---|
| 4,066,902 | 1/1978 | LeMay | 250/363 S |
| 4,066,903 | 1/1978 | LeMay | 250/363 S |
| 4,068,306 | 1/1978 | Chen et al. | 364/414 |
| 4,206,360 | 6/1980 | LeMay | 250/446 T |
| 4,606,004 | 8/1986 | Crawford et al. | 364/414 |
| 4,637,040 | 1/1987 | Sohval et al. | 378/9 |

FOREIGN PATENT DOCUMENTS 0157687 10/1985 European Pat. Off. .
0467532A2 1/1992 European Pat. Off. .
2-23946 1/1990 Japan .

OTHER PUBLICATIONS

IEEE International Symposium on Circuits and Systems, vol. 1, May 1990 U.S., pp. 234–237, Shieh et al.
Reordering Schemes for Multiple-Rotation Fan–Beam CT Scanner, J. Jelinek et al., IEEE Transactions on Medical Imaging, vol. M1-4, No. 4, Dec. 1985.

*Primary Examiner*—Paul M. Dzierzynski
*Assistant Examiner*—David V. Bruce
*Attorney, Agent, or Firm*—Quarles & Brady

[57] ABSTRACT

A CT apparatus for reducing aliasing in reconstructed images uses an x-ray tube with a translatable focal spot to double the spatial sampling rate, over that achieved by a conventional CT machine. Radial resolution artifacts in the image, identified to the "bleeding through" of previous samples from different focal spot positions into the present sample are removed by a convolution process employing the inverse of the detector transfer function. Timing of the data sampling with respect to the changing of the wobble positions is also employed to minimize the bleed through and to improve signal-to-noise ratio.

6 Claims, 3 Drawing Sheets

DECONVOLUTION FILTER FOR CT SYSTEM

BACKGROUND OF THE INVENTION

This invention relates to computed tomography (CT) systems and specifically to a CT system with rotating tube and detector having an x-ray tube whose focal spot may be controllably translated along the plane of the CT gantry rotation.

CT Imaging

In a computed tomography system, an x-ray source is collimated to form a fan beam spreading within a defined fan beam angle. The fan beam is oriented to lie within the x-y plane of a Cartesian coordinate system, termed the "imaging plane", and to be transmitted through an imaged object to an x-ray detector array oriented also within the imaging plane.

The detector array is comprised of detector elements, having centers spaced by a "pitch" distance, each of which measures the intensity of transmitted x-ray radiation along a beam projected from the x-ray source to the particular detector element. The intensity of the transmitted radiation is dependent on the attenuation of the x-ray beam along that beam by the imaged object. The center of a beam and its intensity measurement may be identified to a ray described by the line joining the focal spot of the x-ray source and the center of the detector element.

The x-ray source and detector array are rotated on a gantry within the imaging plane and around the imaged object so that the angle at which the fan beam intersects the imaged object may be changed. At each such gantry angle, a projection is acquired comprised of the intensity signals from each of the detector elements. The gantry is then rotated to a new angle and the acquisition process is repeated to collect a number of projections along a number of gantry angles to form a tomographic projection set.

The acquired tomographic projection set is typically stored in numerical form for computer processing to "reconstruct" a slice image according to reconstruction algorithms known in the art. A projection set of fan beam projections may be reconstructed directly into an image by means of fan beam reconstruction techniques, or the intensity data of each projection may be sorted into parallel beams and reconstructed according to parallel beam reconstruction techniques. The reconstructed tomographic images may be displayed on a conventional CRT tube or may be converted to a film record by means of a computer controlled camera.

Spatial Resolution

The spatial resolution of the reconstructed CT image is dependant, in part, on the width of each x-ray beam at the center of the imaged object. This beam width is determined primarily by the size of the focal spot of the x-ray tube, as collimated, and aperture of the detector element, and varies with the distance from the source and detector. For practical purposes, the averaging effect of a generally rectangular beam of width a, bandlimits the received image to spatial frequencies of $1/a$ and less. The exact bandlimit may be precisely determined by methods understood to those of ordinary skill in the art.

The beam spacing, defined as the center to center separation of the beams near the center of the imaged object, and as determined by the detector pitch, controls the spatial sampling frequency of the CT system. Given the spatial bandlimit of $1/a$, above, the sampling frequency must be greater than $2/a$, per the Nyquist sampling theorem, to avoid aliasing effects in the reconstructed image. A conventional third generation CT scanner samples the scan field with a sample distance equal to "a", thus the sample frequency is only $1/a$ while the Nyquist theorem requires a sampling frequency of at least $2/a$. Sampling at $2/a$ will henceforth be referred to as double sampling.

A conceptually simple way to accomplish double sampling is to shift the detector elements one-half of their pitch after a first sample and to take a second sample while holding the x-ray source in the same position. In this way each beam is sampled twice in its width (and spacing). Nevertheless, the mechanical problems incident to rapidly and precisely moving the detector elements by one-half their pitch (typically on the order of 1 mm) make this approach impractical. Rather, two other methods are used:

Quarter Detector Offset

The first method is to offset the detector elements in the plane of gantry rotation one quarter of the detector's pitch with respect to the gantry's axis of rotation. Beams projected through the imaged object at angles separated by 180° will be offset from each other by one-half of the detector pitch and hence by one-half the beam spacing for an optimized beam.

Although this method is relatively simple, it is only effective near isocenter for fan beam scanning and rapidly degrades with radial distance from isocenter. It also requires a full 360° of scanning and hence is not usable with reduced angle scanning techniques that acquire less than 360° of scanned data. Further, for this method to work properly, the imaged object must not move in between the acquisition of data for each offset beam. The length of time needed for the gantry to rotate 180° may be on the order of a second or more and hence motion of the imaged object is inevitable especially for organs such as the heart.

Focal Spot Wobbling

The second method of performing double sampling of each beam is to "wobble" the x-ray source by an amount that will shift each beam by one-half its spacing. Wobbling is mechanically equivalent to taking a second set of projections with the detector shifted to some odd multiple of one-half of its pitch. In fact, the detector is allowed to naturally rotate to a one-half pitch position while the source is repositioned, along the source's circumferential path of rotation, back to where the projection for the first set was collected. The wobbling is generally within the plane of rotation of the gantry and along the tangent to the gantry rotation. Wobbling of the x-ray source is easily accomplished electronically without mechanical motion of the x-ray tube. In an x-ray tube, an electron beam is accelerated against an anode at a focal spot to produce x-ray radiation emanating from the focal spot. The focal spot may be moved on the surface of the anode by the use of deflection coils or plates within the x-ray tube which deflect the electron beam either by the creation of a local magnetic or electrostatic field as is well understood in the art.

Double sampling using focal spot wobbling may be performed by taking a first set of data with the x-ray spot in a first position on a first 360° scan; and taking a second set of data with the focal spot shifted to a second position on a second 360° scan. Preferably, however, to avoid motion problems between adjacent samples, the x-ray beam is rapidly shifted from one position to the other between each projection.

Unfortunately, the rate at which the x-ray beam can be wobbled may be severely limited by the acquisition speed of the detector elements. This acquisition speed is dependant primarily on the response time of two elements: the detector itself and the low pass filter that is used to achieve the desired signal-to-noise ratio of the projection data. The detector response time is the time required for the signal from the detector to return to zero after stimulation of the detector by x-ray radiation. The detector response is generally a function of the detector design.

Clearly, if the x-ray beam is wobbled faster than the detector signal decays, then the signal obtained at a given wobbled position will be contaminated by the decaying signal from the previous wobbled position. This contaminating signal will be termed the "residual signal". Although some contamination between the sequential signals by the residual signal may be tolerated, as the rate of wobbling increases the contamination increases and produces radial resolution degradation of the tomographic image.

SUMMARY OF THE INVENTION

The present invention provides a method of reducing the residual signal during focal spot wobbling, caused by the intrinsic delay of the detector elements and subsequent data acquisition filters.

Specifically, in a system having a wobbled x-ray source and a detector with a transfer function F(s), the intensity signal from the detector is convolved with a deconvolution vector d(t) referenced to the wobbling of the x-ray source. The deconvolution vector d(t) is the inverse Laplace transform of a function of 1/F(s).

It is one object of the invention to eliminate the degradation of the image's radial resolution caused by the residual signal when the focal spot is wobbled. The deconvolution effectively eliminates the delay caused by the detector's transfer function F(s) and thus prevents residual signal from a previous focal spot position from bleeding into a subsequent intensity signal. This object, of course, is equivalent to allowing a faster wobbling speed while preserving a constant level of spatial resolution.

In one embodiment, the deconvolution vector d(t) is equal to 1/(F(s)G'(s)), where F(s) and G'(s) are non-zero in the system passband and where G'(s) is the undesired portion of the transfer function of a low-pass data acquisition filter. The low pass filter, G(s), is a convenient substitute for an integrator over the system sampling period, and G'(s) is that portion of G(s) that causes signal spillover into subsequent sample intervals.

Thus, it is another object of the invention to eliminate the residual signal caused not only by the delay in the detector, F(s), but also caused by other elements in the signal chain such as the low-pass data acquisition filter which is required prior to sampling and digitizing the intensity signal for later computer processing.

The sampling of the detector signals is timed to maximize the component of the detector signal contributed by x-rays from the desired focal spot position. Accordingly, the sampling of the detector signal is taken at time $\tau$ after the x-ray focal spot has shifted between locations, where $\tau$ equals $\phi + \frac{1}{2}\omega$ and where $\phi$ is the frequency of the wobbling and where $\phi$ is the group delay time associated with the detector signal chain.

Thus, it is yet another object of the invention to reduce the relative effect of the residual signal by appropriate timing of the sampling of the detector signal independent of the subsequent convolution.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Figure 1:
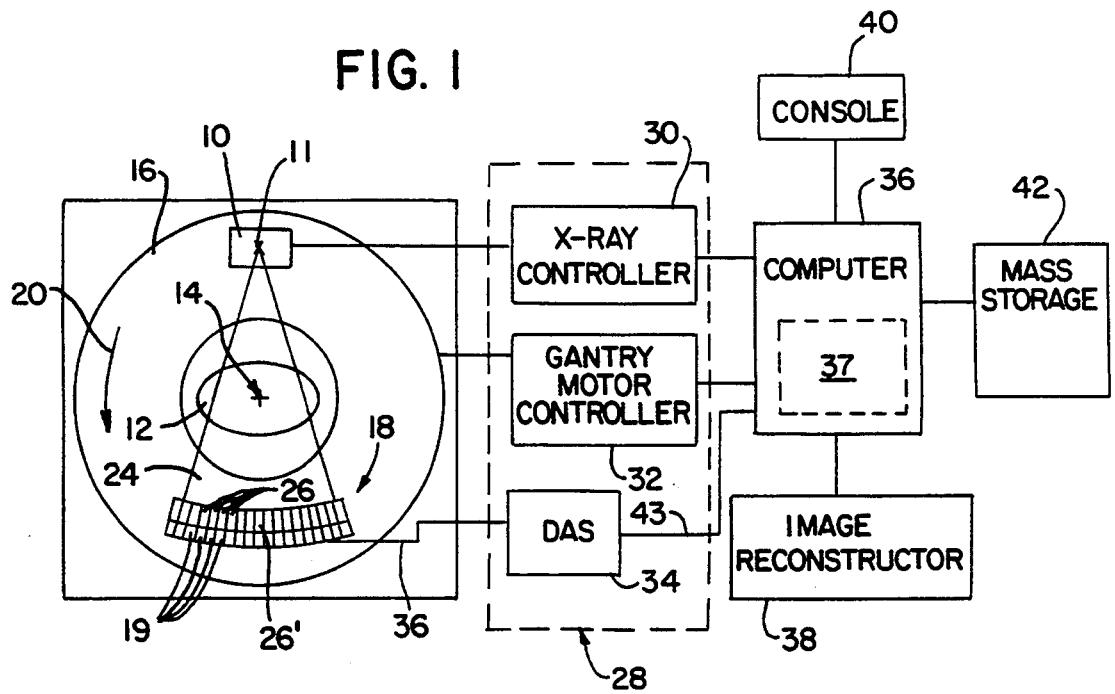
FIG. 1 is a schematic representation of a CT system suitable for use with the present invention.

Referring to FIG. 1, a CT gantry 16, used in a "third generation" CT scanner, holds an x-ray source 10 oriented to project a fan beam of x-rays 24 from a focal spot 11 through imaged object 12 to detector array 18. The detector array 18 is comprised of a number of detector elements 26 which together detect a projection resulting from the transmission of x-rays 24 through the imaged object 12. The signals from the detector elements 26 are received by filters 19 to be described in more detail below. A center detector element 26' is positioned midway along the length of the array 18 to generally align with a ray (not shown) from the focal spot 11 through the center of rotation 14. The gantry 16 rotates about a center of rotation 14 positioned within the imaged object 12.

The control system of a CT scanner, suitable for use with the present invention, has gantry associated control modules 28 which include: x-ray controller 30 which provides power and timing signals to the x-ray source 10 and which controls the position of focal spot 11 within the x-ray tube, gantry motor controller 32 which controls the rotational speed and position of the gantry 16, and the data acquisition system (DAS) 34 which receives projection data as an intensity signal 36 from the detector array 18, through the filters 19, and converts the signal 36 to digital words 43 for later computer processing.

The x-ray controller 30 and the gantry motor controller 32 are connected to a computer 36. The computer 36 is a general purpose minicomputer such as the Data General Eclipse MV/7800C and may be programmed to synchronize the acquisition of intensity signals from the detector elements 26 with the position of the focal spot 11 per the present invention as will be described in detail below. Computer 36 includes high speed random access memory 37 which is used to store the digital words 43 from the DAS 34 and for subsequent processing of that data as will be described below.

The DAS 34 is connected to the computer memory 37 which receives sampled and digitized signals from the detector array 18 via the filters 19. An image reconstructor 38 operates on the projection data in memory 37 to perform high speed image reconstruction according to methods known in the art. The image reconstructor 38 may be an array processor such as is manufactured by Star Technologies of Virginia.

The computer 36 receives commands and scanning parameters via operator console 40 which is generally a CRT display and keyboard which allows an operator to enter parameters for the scan and to display the reconstructed image and other information from the computer 36. A mass storage device 42 provides a means for storing operating programs for the CT imaging system, as well as image data for future reference by the operator.

Figure 2:
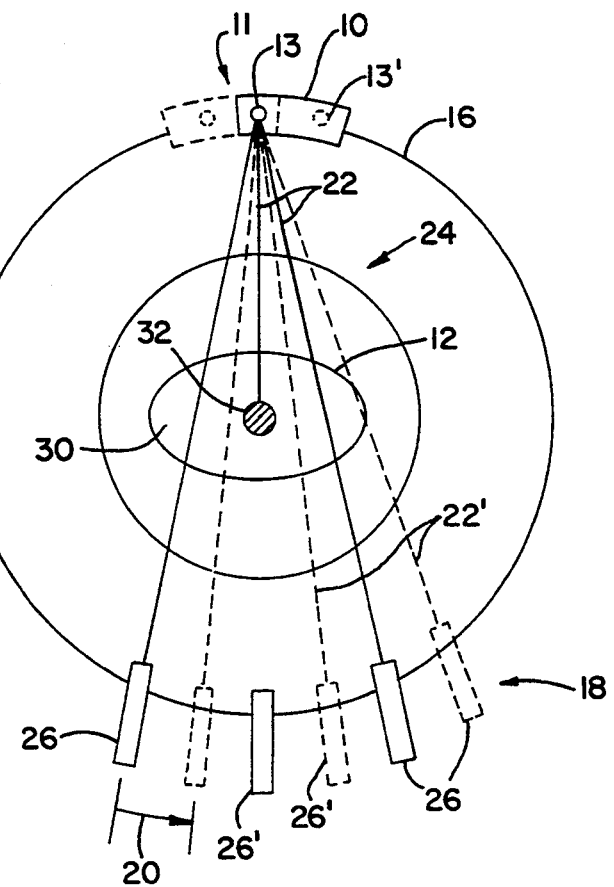
FIG. 2 is a detail of the fan beam of x-rays produced by the system of FIG. 1 showing the improved sampling resolution produced by focal spot wobbling and showing one beam that is occluded for one focal spot position only.

Referring to FIG. 2 the focal spot 11 of x-ray source 10 may be moved with respect to the gantry 16 between a first focal spot position 13 and a second focal spot position 13' where focal spot position 13' is displaced tangentially to the rotation 20 of the gantry 16. At each focal spot location 13 or 13', the detector elements 26 produce an intensity signal dependent on the absorption of the x-ray fan beam 24 along rays 22 from the x-ray focal spot 11 to the center of the particular detector element 26.

The distance between focal spot positions 13 and 13' is chosen so that the rays 22 are shifted by approximately half the beam spacing, for a movement of focal spot 11 between position 13 and 13', as measured near the center of the imaged object 12. As previously described, the beam spacing is determined by the angular separation of the rays 22 as controlled by the spacing of the detector elements 26.

The frequency of the wobbling of the focal spot 11 with respect to the speed of the gantry is chosen so that the rotation 20 of the gantry 16 causes the rays 22 to compliment previous or later acquired projection data along rays 22'. An appropriate relationship between the rotation of the gantry 20 and the movement of the focal spot 11 between positions 13 and 13' is described in detail in copending application Ser. No. 07/540,995 filed Jun. 20, 1990, entitled: Computed Tomography System with Translatable Focal Spot, assigned to the same assignee as the present invention and hereby incorporated by reference.

Referring still to FIG. 2, an example imaged object 12, comprises a homogeneous attenuating medium 30 having an x-ray opaque inclusion 32. Pet this example, the size and placement of the inclusion 32 is such that a ray 22 to a center detector element 26' is blocked entirely when the focal spot 11 is in position 13 and not blocked when the focal spot is in position 13' after rotation of the gantry 16. Thus, the detector signal from center detector element 26' varies with motion of the focal spot 11 between low attenuation and complete attenuation.

Figure 3:
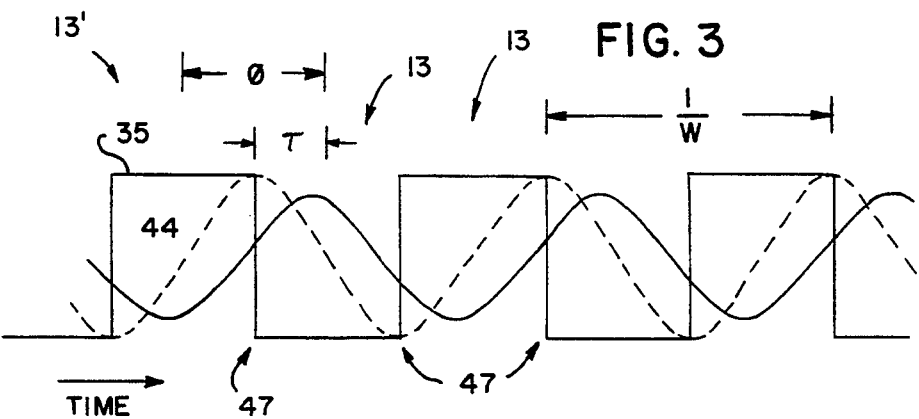
FIG. 3 is a graph showing focal spot position and a corresponding intensity signal for the occluded beam of FIG. 2 before correction by the present invention and, in phantom, after correction by the present invention.

Referring now to FIG. 3, square wave, wobble signal 35 indicates the motion of the focal spot between positions 13 to 13', with position 13' being indicated by the high state of wobble signal 35 and position 13 being indicated by the low state of wobble signal 35. Wobble signal 35 reflects the signal produced by the x-ray controller 30 to move the focal spot 11 between its two positions 13 and 13'.

An intensity signal 36, produced by the center detector element 26', indicates the change in the intensity of the x-rays received by the center detector element 26' as the opaque inclusion 32 blocks or transmits ray 22 to the center detector element 26'. As a result of the integrating nature of the detector element 26' and the finite flux rate of the x-rays source 11, the intensity signal 36 builds slowly to follow the wobble signal 35 when the focal spot 11 changes position. Further, the transfer function of the detector element 26', F(s), as will be described in detail below, bandlimits the detector signal 36 to have a sine-like shape, resulting from its loss of high frequencies, and delays the peak of the detector signal 36 in phase by an angle $\phi$.

The effect of the attenuation and phase shift on the intensity signal 36 may be easily identified and compensated for in the present example where the x-ray beam along ray 22 is completely obscured for the focal spot positions 13. In general, however, both focal spot positions 13 and 13' will contribute a component of the intensity signal 36 and the group delay of the detector elements 26 cause these contributions to bleed together at any given point in time.

Thus, referring to FIG. 5, in most circumstances, the intensity signal 36 will be made up of a combination of component signals 54 and 58 produced by the current and previous x-ray exposure of detector element 26' at the different focal spot positions 13 and 13'. Generally, intensity signal 36 includes many component signals 58 associated with a number of previous cycles of the wobble signal 35. As will be discussed, however, for practical purposes, it is assumed that the component signals 58 are from only a limited number of cycles of wobble signal 35.

Figure 4:
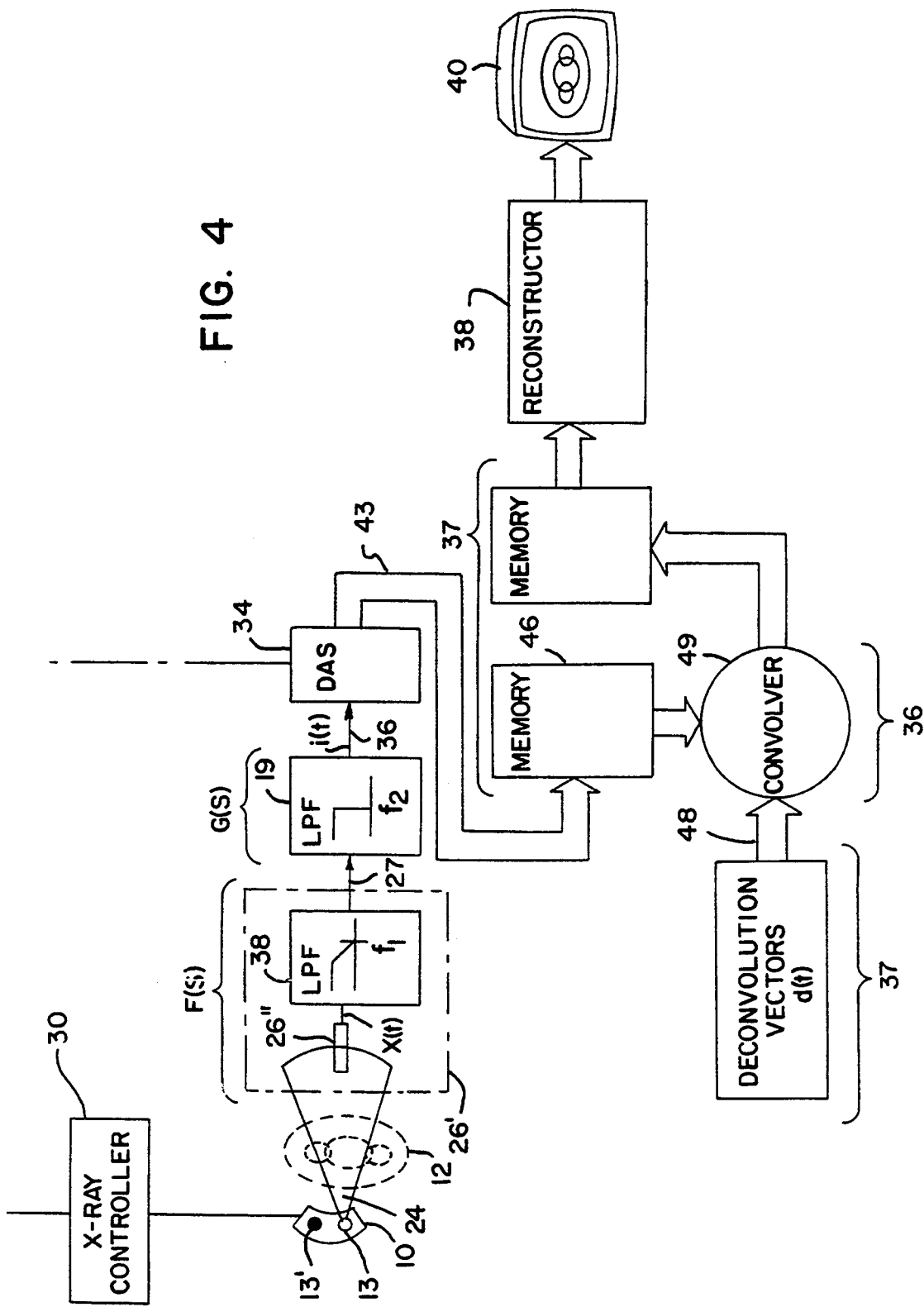
FIG. 4 is a block diagram of the convolution process of the present invention for correcting the uncorrected intensity signal of FIG. 3.

Referring now to FIGS. 1 and 4, the signal chain for the CT system begins with the x-ray source 10 which produces a fan beam of x-rays 24 emanating alternately from positions 13 or 13' as the focal spot 11 is wobbled. Fan beam 24 is attenuated by the imaged object 12 and received by the plurality of detector elements 26 including center detector element 26'. The detector signals 27 from each detector element 26 are received by filters 19 producing an intensity signal 36 received by the DAS 34. DAS 34 samples the intensity signal 36 at a sampling frequency $\omega$ and converts the sampled data points into digital words 43 that are stored in the memory 37 of computer 36 for later processing.

The filters 19 are low-pass data acquisition filters which substitute for integrators over the DAS sample interval to improve the signal-to-noise ratio of the detector signal 27. Such low-pass data acquisition filters 19 are well-known in the art and require bandlimiting the detector signal 27.

Each of the elements of the above described signal chain may be described by a transfer function. Of particular interest is F(s), the response of the detector elements 26 which may be measured and then modeled as an ideal detector element 26" followed by a filter 38 having the transfer function F(s) representing the real world deviation of the detector elements 26 from the ideal detector element 26". The output signal of the ideal detector element 26" will be designated x(t).

The transfer function F(s) is the Laplace transform of the function relating the output of the detector element 26, an electrical current, to the input of the detector element 26', an x-ray flux. As is understood, the Laplace transformation is a mathematical method of converting complex differential equations into more convenient algebraic equations. In the transformation, the complex variable "s" is substituted for the time variable "t" and hence the time domain transfer function f(t) of the filter 38 becomes F(s).

As a result of this Laplace transformation, the transfer functions for various elements of the signal processing chain including filters 38 and 19 may be simply multiplied together to obtain the overall transfer function of the signal chain.

Referring still to FIG. 4, for a detector element 26' constructed from a crystal scintillator, the transfer function of the filter 38 may be approximated as a single pole, low-pass filter having a cut-off frequency of $f_1$ as determined by measuring the detector response. Such a filter may be readily modeled mathematically, and the value of its transfer function F(s) derived from this model.

As described, the intensity signal produced by the detector element 26' is received by DAS 34 which is a sampling digital-to-analog converter preceded by a low-pass data acquisition filter 19. In the preferred embodiment, the low-pass data acquisition filter 19 is a three pole, low-pass filter with a cut-off frequency of $f_2$ determined by signal-to-noise considerations as mentioned above. The transfer function of this low-pass data acquisition filter 19 is also readily determined by the model of this filter and is designated G(s).

The effects of the transfer functions F(s) and G(s) on the intensity signal 36, as shown in FIG. 3, are that of group delay and attenuation, and these effects may be eliminated by creating a transfer function D(s) where:

$$D(s) = \frac{1}{F(s)G(s)} \quad (1)$$

for F(s) and G(s) which are non-zero in the system passband.

Thus the overall transfer function of the signal chain including a filter having a transfer function D(s) would be:

$$F(s)G(s)D(s) = F(s)G(s)\frac{1}{F(s)G(s)} = 1 \quad (2)$$

This approach is not used, however, because it cancels the desired integrating effect of the low-pass data acquisition filter 19 of improving signal-to-noise ratio. Hence D(s) is computed using a modified transfer function G'(s) that incorporates only the undesirable aspects of G(s) that cause signal spillover into subsequent sample intervals. Specifically,:

$$D(s) = \frac{1}{F(s)G'(s)} \quad (3)$$

The modification of G(s) to produce G'(s) is accomplished by dividing G(s) by a modifying function U(s):

$$G'(s) = \frac{G(s)}{U(s)} \quad (4)$$

U(s) is the transfer function of a mathematically ideal low-pass data acquisition filter, having generally the proper integration characteristics over the sample interval without the undesired delay. In the preferred embodiment, U(s) is determined by considering a square-wave at frequency $\omega$ having a well defined transform X(s) and the desired output Y(s) after passing through the low-pass data acquisition filter. Output Y(s) is chosen to be the well defined transform of a triangle wave also at frequency $\omega$ and in phase with X(t) since this is the response of an integrator to a square wave input. It will be understood that other transfer functions U(s) produced by considering other inputs and outputs X(s) and Y(s) may be used in place of those described above.

Ideally then, the intensity signal 36 when operated on by transfer function D(s) provides an intensity signal x(t) equal to that produced by the ideal detector element 26". In practice, however, the intensity signal 44 (shown in FIG. 3) produced by the operation of the inverse transfer function D(s) still exhibits the frequency loss caused by transfer functions F(s) and G'(s) to the extent that these frequency components were for practical purposes reduced to zero and therefore irrecoverable. Nevertheless, the reverse transfer function D(s) eliminates the lag of the intensity signal 36, except that caused by the integration of the ideal detector element 26", and eliminates the attenuation of that signal.

The multiplication of the intensity signal 36 by the inverse transfer function D(s) is accomplished in practice by convolving the time domain intensity signal 36, i(t), as sampled by the DAS 34 and stored in memory 37, by a time domain version of D(s) designated d(t) and termed the deconvolution vector. It will be recognized that the use of the notation of the Laplace transformation is for descriptive convenience and that other well known and equivalent mathematical techniques may be used to derive the function d(t). This ability to effect the inverse transfer of D(s) in the time domain stems from a Laplace transform theorem that relates multiplication of Laplace transforms, i.e. multiplication of the transfer functions F(s), G'(s) and D(s), to convolution of the time domain signals f(t), g(t) and d(t), where the time domain signals are simply the inverse Laplace transform of the transfer functions.

Convolution, a well-known mathematical operation, involves the integration of a multiplication of the two waveforms. The convolution of the intensity signal 36, i(t), and the deconvolution vector d(t) produces the signal x(t) from the ideal detector element 26" as follows:

$$x(t) = \int_{-\infty}^{+\infty} i(\lambda)d(t - \lambda)d\lambda \quad (5)$$

where $\lambda$ is a dummy variable of integration spanning the deconvolution vector d(t), and x(t) is evaluated at the moments of change in position of the focal spot 11 between 13 and 13' or points 47 as shown in FIG. 3.

It will be understood to those of ordinary skill in the art that deconvolution typically requires an over-sampling of the signal to be deconvolved (i.e. a sampling rate much in excess of the Nyquist rate) and the deconvolution of a large number of samples with a correspondingly lengthy deconvolution vector. Such oversampling and extended deconvolution, in the context of a CT system where fast reconstruction time is demanded, would require impractical increase in computational speed and cost.

The present invention is founded on the discovery, through experiments conducted with computer simulations, that the deconvolved signal does not need to be over-sampled nor is a lengthy deconvolution vector required to achieve a meaningful reduction in the resolution degradation caused by focal spot wobbling.

In practice, equation (5) is simplified by limiting the amount of data i(t) convolved. Referring to FIG. 5, the intensity signal 36 for detector element 26' is sampled at point 56, a time $\tau$ after the transition of the focal spot 11' between positions 13 and 13' as shown by wobble signal 35 and to be described further below. Depending on the low-pass filter, the contributions to the intensity signal 36, at point 56, from previous component signals 58 diminishes rapidly (for example, within five samples) with the length of time preceding point 56. Therefore, data from the intensity signal 36 is collected for convolution with only a limited number of wobble samples 35. Four samples of the intensity signal 36 are taken by the DAS 34 at sample periods 52 for each cycle of wobble signal 35 for a given detector element 26 and hence only five samples of data for i(t) are used: the sample at point 56 and four previous samples.

The limited number of samples of the intensity signal i(t) limits the necessary number of data points required in the deconvolution vector d(t) to an equal number: five, it also limits the amount of overscan data needed to support deconvolution of the end point samples.

The deconvolution vector d(t) is evaluated at specific points in time corresponding to the points in time at which the intensity signal 36 is sampled, and is stored in memory 37.

Equation (5) is evaluated only at a single time $t_0$, the time when the focal spot 11 changes between positions 13 and 13' as shown in FIG. 3. Time $t_0$ is the expected maximum for the waveform 44 of the ideal detector element 26.

The discrete version of convolution of equation (5) may be performed on the digital words 43 as stored in the computer memory 37 and requires multiplying the values of the digital words 43 by values 48 of the corresponding deconvolution vector d(t), each indexed by integer $\lambda$ values between limits spanning the finite i(t) and d(t), and the summing of those products, as indicated by convolver block 49. The convolver 49 is implemented by the computer 36 as will be understood to those of ordinary skill in the art.

The step of subtracting $t_0-\lambda$, for indexing the values of d(t), required in equation (6) may be eliminated by simply storing the deconvolution vector in its offset form $d'(t)=d(t_0-\lambda)$ and multiplying $i(\lambda)$ by $d'(\lambda)$.

Figure 5:
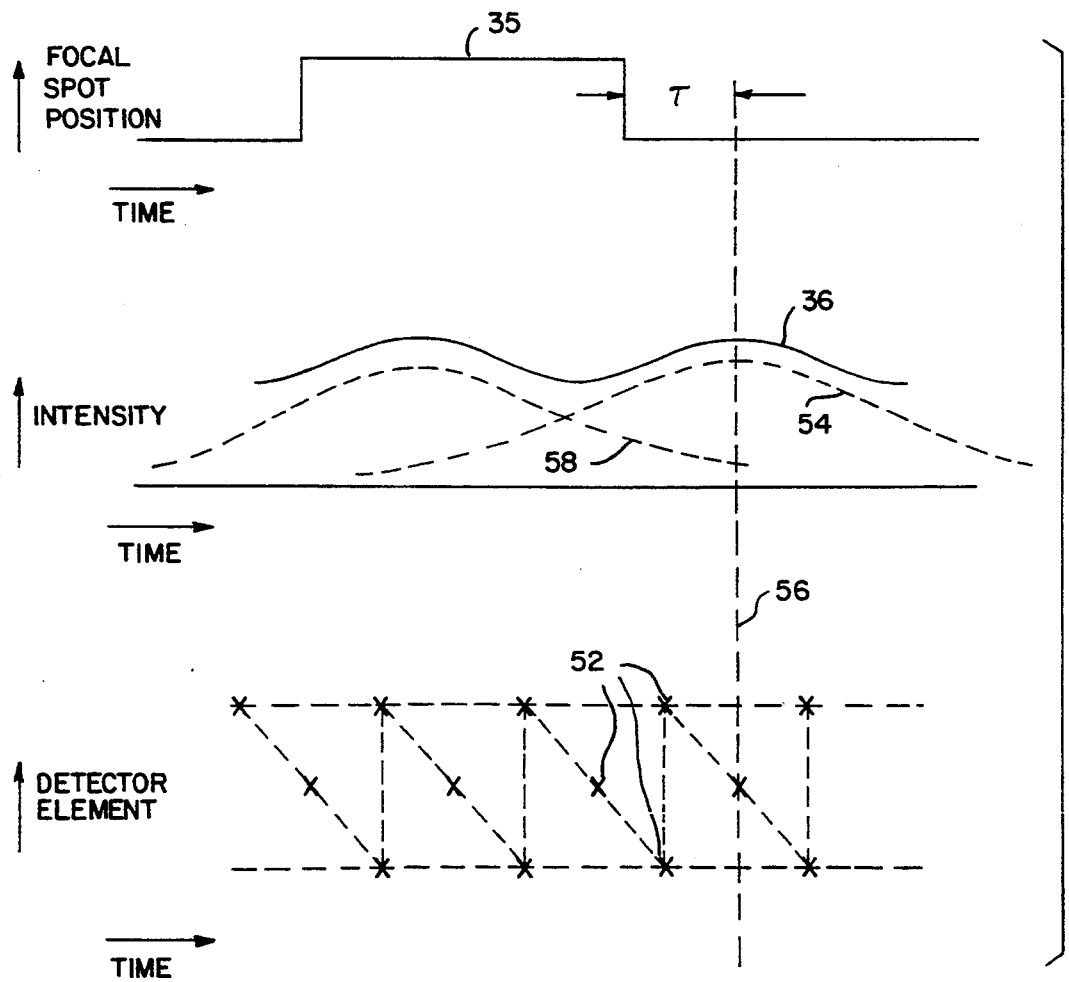
FIG. 5 is a plot of the focal spot position similar to FIG. 3 showing the timing of the sampling of the detector's intensity signals with respect to the focal spot position, and showing the contribution of the component signals of each focal spot position, to the resulting intensity signal.

Referring to FIG. 5, in the preferred embodiment, a DAS 34 (shown in FIG. 4) is multiplexed among a number of detector elements 26 and hence the sampling point for the intensity signals 36 for various detector elements 26 will be staggered in time about the sampling point 56 for the center detector element 26'. Only the sampling points 56 of the detector elements 26 at the ends of the detector array 18 and its center are shown. Even though each of the convolved signals for each detector element 26 is evaluated at the same time $t_0$, multiple deconvolution vectors d(t) will be required to convolve the intensity signals 36 for different detector elements 26 because the range of samples of i(t) for each intensity signal 36 for each detector element 26 will be offset from the others, and the exact instant of the sampling will also be offset. The generation of the multiple deconvolution vectors may be accomplished by interpolating between a set of master deconvolution vectors of high resolution and offsetting the points in time at which the devolution vector d(t) is evaluated for storage in memory 37.

Referring still to FIGS. 3 and 5, the timing of the samples taken by DAS 34 with respect to the wobble signal 35 is also critical in maximizing the signal-to-noise ratio of the resulting image data. The idea is to time the samples to occur at the crest and valley of signal 36 to minimize the contamination between wobble positions since this will require a less intense deconvolution function and hence a better signal-to-noise ratio. As discussed, in the preferred embodiment, the sampling of each detector element 26 by DAS 34 is performed in a serial fashion with the sampling periods 52 for the detector elements 26 at one edge of the array 18 occurring before the sampling period 52 of the center detector element 26' and followed by the sampling period 52 for the detector elements 26 at the other edge of the detector array 18.

The signal-to-noise ratio of deconvolved signal x(t) is maximized by sampling the intensity signal 36 at the crest of the component signal 54 after the conclusion of the detector's integration over the previous focal spot position. Specifically, the sampling should occur at a time after the change in focal spot position, indicated by wobble signal 35, equal to the delay caused by the transfer function F(s)G(s). This crest occurs at a point 56, time $\tau$ after the change in wobble states indicated by wobble signal 35 and is equal to the group delay caused by the transfer functions F(s) and G(s).

This group delay may be approximated by the phase or group delay $\phi$ produced by those transfer functions F(s) and G(s) at the wobble frequency of the wobble signal 35. Specifically, the crest may be assumed to lie at time $\tau$ after the transition of the wobble signal 35 at 47 where $\tau=\phi+1/4\omega$ where $\omega$ is the wobble frequency and $\phi$ is the group delay caused by the transfer functions F(s) and G(s) at $\omega$.

The group delay $\phi$ is readily evaluated from the modeled transfer functions F(s) and G(s). As a result of the serial sampling of the detector elements 26 by the DAS 34, only one detector element 26 may be sampled at the optimum point 56, $\tau$ after point 47. The detector chosen to be sampled at this point is the center detector element 26' so as to provide the highest signal quality for the center of the image, which is ordinarily of more diagnostic significance than the edges of the image and to reduce the maximum offset time in the sampling of the edge detector elements 26. Thus, the intensity signal 36 for the center detector element 26' is sampled at point 56 and the intensity signals 36 for the detector elements 26 on either side of the center detector element 26' are sampled before and after point 56.

Even without convolution, sampling at the sampling point 56, or near that point, provides the clearest indication of the value of the component signals 54 associated with focal spot position 11 and referring to FIG. 3, a good approximation of the value of waveform 44 from an ideal detector element 26" at time 47.

In practice, at the sampling point 56, the residual signal from the previous focal spot position 58 may be less than 20% of the signal 36 at sampling point 56, thus providing a significant degree of reduction in the effect of the bleed-through of the residual signal with minimum computational overhead. When the convolution of process block 49 is used, sampling at point 56 provides improved signal-to-noise ratio by maximizing the sampled signal strength.

In summary, the invention addresses the signal spillover, between the measurement periods defined by the wobbling of the focal spot, caused by the circuitry and filtering of the data acquisition chain. The invention results from the determination, made through computer simulations, that the deconvolution technique may be practically implemented with a relatively short deconvolution vector without oversampled data and still achieve significant reduction in the spatial resolution degradation caused by spot wobbling.

Many modifications and variations of the preferred embodiment which will still be within the spirit and scope of the invention will be apparent to those with ordinary skill in the art. In order to apprise the public of the various embodiments that may fall within the scope of the invention, the following claims are made.

We claim:

1. A CT apparatus for imaging a body comprising:
a gantry rotatable about a center within a plane of rotation;
an x-ray source mounted on said gantry for producing x-ray radiation emanating from a first and second location with respect to the gantry, the locations generally within the plane of rotation of the gantry and along a tangent of the gantry rotation;
an x-ray control means for causing the x-rays from the x-ray source to shift at a transition time between the two different locations to produce first and second projection data;
a detector attached to the gantry for receiving the x-ray radiation from the first and second location and comprised of at least one detector element having a transfer function F(s) for producing an intensity signal which is responsive to the transition time; and
a convolution means receiving the intensity signal and responsive to the transition time for convolving the intensity signal with a deconvolution vector d(t) referenced to the transition time wherein the signal d(t) is the inverse Laplace transform of a function of 1/F(s).

2. The CT apparatus recited in claim 1 wherein the signal d(t) is equal to the inverse Laplace transform of 1/F(s).

3. The CT apparatus recited in claim 1 including:
a digital to analog converter for sampling the intensity signal at a sampling rate, and having a low-pass data acquisition filter for filtering the intensity signal prior to sampling, the low-pass data acquisition filter having a transfer function of G(s) having undesirable characteristics G'(s) wherein the signal d(t) is equal to the inverse Laplace transform of $$\frac{1}{F(s)G'(s)}.$$

4. A CT apparatus for imaging a body comprising:
a gantry rotatable about a center within a plane of rotation;
an x-ray source mounted on said gantry for producing x-ray radiation emanating from a first and second location with respect to the gantry, the locations generally within the plane of rotation of the gantry and along a tangent to the gantry rotation;
an x-ray control means for causing the x-rays from the x-ray source to shift between the two different locations at a wobble frequency $\omega$ to produce first and second projection data;
a detector attached to the gantry for receiving the x-ray radiation from the first and second location and comprised of at least one detector element having a transfer function F(s) for producing an intensity signal having a group delay $\phi$; and
a sampling means for sampling the intensity signal at time $\tau$ after the x-ray source has shifted between locations where $\tau$ equals $$\phi + \frac{1}{4\omega}.$$

5. The CT apparatus of claim 4 including:
a convolution means responsive to the x-ray control for convolving the sampled intensity signal with a deconvolution vector d(t) referenced to the shifting of the x-ray source between the first and second positions; and
wherein the signal d(t) is the inverse Laplace transform of a function of 1/F(s).

6. ACT apparatus for imaging a body comprising: is a gantry rotatable about a center within a plane of rotation;
an x-ray source mounted on said gantry for producing x-ray radiation emanating from a first and second location with respect to the gantry, the locations generally within the plane of rotation of the gantry and along a tangent of the gantry rotation;
an x-ray control means for causing the x-rays from the x-ray source to shift between the two different locations at a wobble frequency $\omega$ to produce first and second projection data;
a detector array attached to the gantry and having a plurality of detector elements arranged between two ends within the plane of rotation about a center detector element, for receiving the x-ray radiation from the first and second location and said detector elements having a transfer function F(s) for producing an intensity signal having a group delay $\phi$; and
a sampling means for sampling the intensity signal of each detector in a series from one end of the detector array to the other so that the intensity signal from the center detector is sampled at time $\tau$ after the x-ray source has shifted between locations where $\tau$ equals $$\phi + \frac{1}{4\omega}.$$

* * * * *